United States Patent
Wollenweber

(10) Patent No.: US 6,895,105 B2
(45) Date of Patent: May 17, 2005

(54) IMAGING TABLE SAG MEASUREMENT AND COMPENSATION METHOD AND APPARATUS

(75) Inventor: Scott D. Wollenweber, Waukesha, WI (US)

(73) Assignee: General Electric Company, Schenenctady, NY (US)

( * ) Notice: Subject to any disclaimer, the term of this patent is extended or adjusted under 35 U.S.C. 154(b) by 652 days.

(21) Appl. No.: 09/745,572

(22) Filed: Dec. 21, 2000

(65) Prior Publication Data

US 2002/0081008 A1 Jun. 27, 2002

(51) Int. Cl.[7] .................................................. G06K 9/00
(52) U.S. Cl. ...................... 382/131; 382/130; 382/132; 382/133; 382/291; 600/424; 600/425
(58) Field of Search ................................ 382/130–132, 382/133; 600/424–428; 378/197

(56) References Cited

U.S. PATENT DOCUMENTS

| | | | | |
|---|---|---|---|---|
| 5,482,042 A | * | 1/1996 | Fujita | .......................... 600/428 |
| 6,334,708 B1 | * | 1/2002 | Kosugi | ......................... 378/197 |
| 6,405,072 B1 | * | 6/2002 | Cosman | ...................... 600/426 |
| 6,473,634 B1 | * | 10/2002 | Barni | .......................... 600/425 |
| 6,631,284 B2 | * | 10/2003 | Nutt et al. | ................... 600/427 |

* cited by examiner

Primary Examiner—Bhavesh M. Mehta
Assistant Examiner—Gregory Desire
(74) Attorney, Agent, or Firm—Quarles & Brady LLP; Carl Horton

(57) ABSTRACT

An apparatus and method for use in correcting for table sag within a dual imaging system wherein the dual system includes two separate imaging configurations that define first and second imaging areas arranged sequentially along an imaging axis and that generate first and second imaging data sets, the apparatus including at least one sensor for identifying table sag and a compensator for modifying at least one data set to correct for table sag prior to combining the data sets to form a single image.

22 Claims, 2 Drawing Sheets

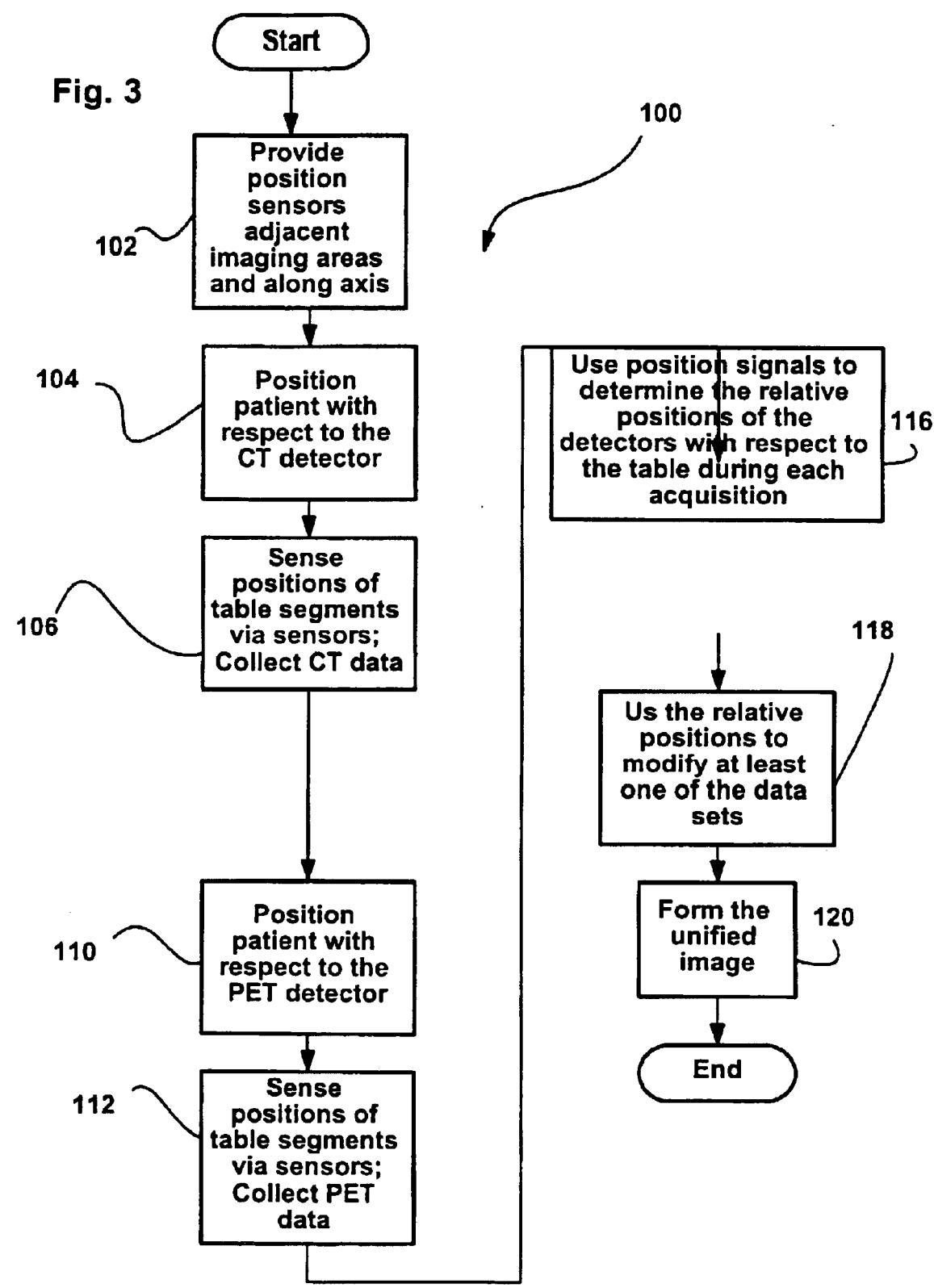

IMAGING TABLE SAG MEASUREMENT AND COMPENSATION METHOD AND APPARATUS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The field of the invention is medical imaging systems and more specifically includes systems for compensating for misalignment of two or more image data sets due to support table deflection.

The medical imaging industry has developed many different types of imaging systems that are useful for diagnostic purposes. Each different system typically has particular uses for which it is advantageous. For example, computerized tomography (CT) systems that employ X-rays are useful for generating static images of bone and the like while positron emission tomography (PET) systems are useful for generating dynamic or functional images of dynamic occurrences such as blood flow and the like.

For various reasons it is advantageous to generate images that include both static and functional characteristics. To this end one solution has been to sequentially use separate imaging systems to gather both functional and static imaging data sets and then combine those sets or corresponding images to generate unified functional/static images. For example, first a CT system may be used to generate a CT image and second a PET system may be used to generate a PET image, the two images being combined thereafter to generate the unified image.

Unfortunately, systems having two separate imaging configurations have several shortcomings. First, there has to be some way to align the functional and dynamic images so that the unified image reflects relative anatomical positions precisely. To this end fiducial markers have been employed. For example, a metallic button with a positron emitter can be placed on the surface of a patient's skin which is detectable by both the CT and PET systems. By aligning the marker in the resulting images the images can be aligned.

Second, where two separate imaging configurations are employed a patient has to be moved from one configuration to the next between acquisition sessions. Movement increases the likelihood that the patient's positions during the two imaging sessions will change thus tending to reduce the possibility of accurate alignment (i.e., relative positions of organs or the like could change during movement). The possibility of misalignment is exacerbated by the fact that often imaging session schedules will not allow both CT and PET imaging processes to be performed during the same day. Thus, overall diagnostic value of the resulting unified image can be reduced appreciably through movement between acquisition periods.

One solution to eliminate the need to move patient's between acquisition periods is to provide a dual CT-PET imaging system like the one illustrated in FIG. 1. In these types of systems both a CT imaging configuration 14 and a PET imaging configuration 16 are arranged sequentially along a single translation axis 19 with their relative positions fixed. A support 12 for a support table 18 is positioned adjacent the system with the table 18 moveable along the translation axis 19. Here the CT and PET systems can be used simultaneously or sequentially to acquire both CT and PET sets of imaging data in a relatively short time and without moving the patient from one configuration to another. The end result is less patient movement, less time to gather required data and better alignment of resulting images to provide a more accurate unified image.

One problem with dual imaging systems is that each of the CT and PET configurations typically include a gantry to support a detector or series of detectors laterally displaced from the translation axis 19. For this reason the translation axis 19 is relatively long and the support table 18 needs to extend a relatively long distance in order to accommodate the system configurations.

While every effort is made to provide stiff supports and tables so that vertical alignment within CT and PET imaging areas can be maintained, when a patient is positioned on a table and the table is extended to accommodate the axial length of dual imaging systems it has been found that the tables often sag such that the CT and PET data sets collected are not aligned along the translation axis 18. Exacerbating matters is the fact that over time stiffness of some supports and tables has been known to deteriorate. While stiffer tables and supports is an option, increased stiffness is a relatively expensive proposition as exotic configurations and materials have to be used to achieve greater stiffness.

BRIEF SUMMARY OF THE INVENTION

An exemplary embodiment of the invention includes an apparatus wherein at least one sensor senses, during data acquisition with a support table extended, the position of the table, a determiner uses the table position signals to determine the relative positions of the first and second detectors (corresponding to first and second imaging configurations such as a CT configuration and a PET configuration, respectively) with respect to the table and a compensator uses the relative positions to modify at least one of the data sets prior to the sets being combined to form a unified image.

In one embodiment the apparatus includes two sensors so that two table segment positions can be tracked during data acquisition and both table position signals can be used to modify the data set. In another embodiment both the first and second data sets can be modified as a function of the table position signals.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

BRIEF DESCRIPTION OF THE SEVERAL VIEWS OF THE DRAWINGS

FIG. 3 is a flow chart illustrating one method according to the present invention.

DETAILED DESCRIPTION OF THE INVENTION

Figure 1:
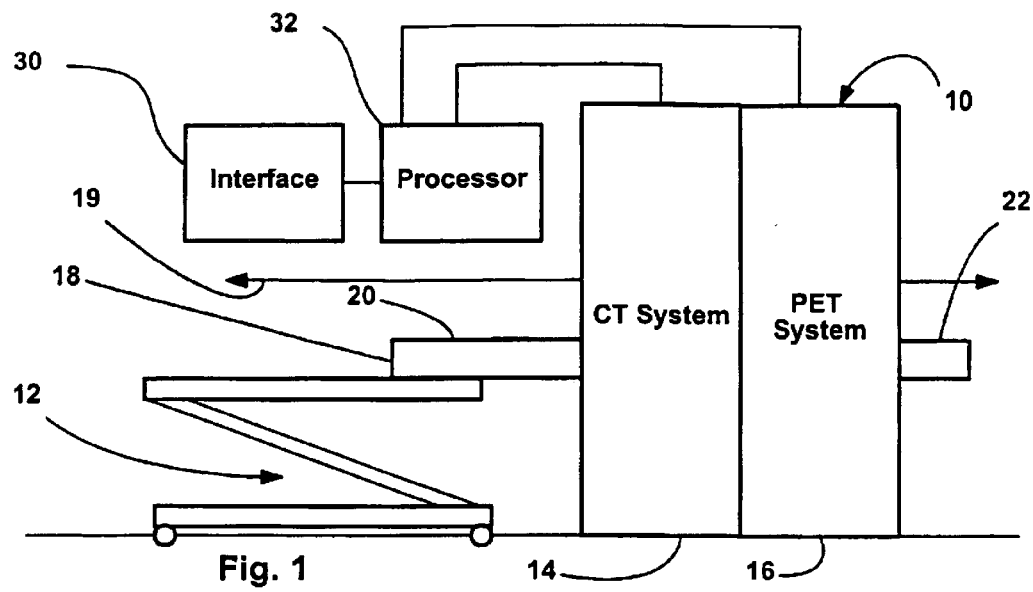
FIG. 1 is a schematic view of a prior art combined CT-PET imaging system.
Figure 2:
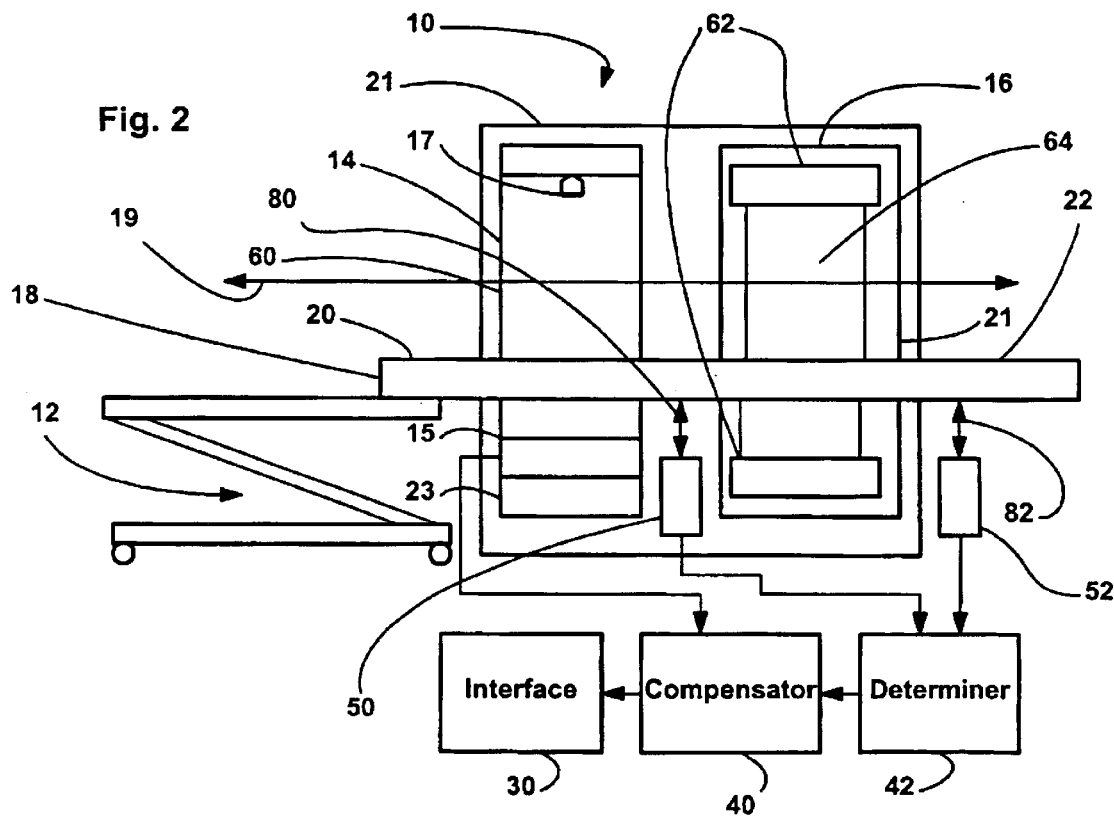
FIG. 2 is a schematic view of the present invention including two separate table position sensors.

Referring now to the drawings wherein like reference numbers indicate similar components throughout the several views and, more specifically, referring to FIG. 2, therein is illustrated an exemplary embodiment of the present invention in the context of a combined CT-PET imaging configuration 10. Configuration 10 generally includes a support 12, a table 18, an imaging system 21, first and second sensors 50, 52, respectively, a determiner 42, a compensator 40 and an interface 30. Support 12 is similar to the various types of table supports known in the art and therefore will not be described here in detail. Similarly, table 18 is similar to known tables and therefore will not be described here in detail. Suffice it to say that table 18 is mounted on top of support 12 for motion in at least the direction along the length of table 18. When used in conjunction with imaging system 21, table 18 can be stepped along a translation axis 19 defined by system 21 as described in more detail below.

System 21 includes both a CT imaging configuration 14 and a PET imaging configuration 16. CT configuration 14 includes a CT detector array 15 and an opposing source 17 mounted for rotation about a gantry 23. The space between source 15 and detector 17 defines a CT imaging area 60. Similarly, PET system 16 includes oppositely facing PET detectors collectively referred to by numeral 62 that, when rotated about a PET gantry 21 define an annual PET imaging area 64. The CT and PET configurations 14, 16, respectively, are in a fixed position with respect to each other and such that the imaging areas 60 and 64 are adjacent and spaced along translation axis 19. As illustrated, when table 18 is moved into and through imaging areas 60 and 64 in a direction parallel to axis 19, a first segment or end 22 of table 18 first passes through imaging area 60 and then through area 64 while end 20 of table 18 remains secured to support 12.

It should be appreciated from FIG. 2 that, when table 18 is extended as illustrated, table 18 tends to sag or deflect downward at extended end 22. This is particularly true in the case of relatively large patients that may have to be supported by table 18. Thus, because table 18 deflects downward, when CT data is acquired via configuration 14, the relative vertical position of the portion of the patient being imaged will be at a first height, whereas, when the table is extended further so that the same portion of the patient is imaged via PET configuration 16, the portion imaged will be at a relatively lower height. In addition, assuming that a patient's head is positioned at end 22 of table 18, when the table is extended such that the portion of the patient being imaged is moved from within CT imaging area 60 to imaging area 64, table 18 will likely deflect even more as additional weight is located further from end 20. Thus, in addition to the portion of the patient being imaged being at a lower vertical position, that portion will also be skewed downwardly. In this case, clearly the CT data collected for the portion of the patient being imaged will not be aligned with the PET data collected.

To compensate for the misalignment of the CT and PET data, referring still to FIG. 2, in one embodiment of the invention first and second table position sensors 50 and 52 are provided adjacent the translation axis 19 and outside the imaging areas 60 and 64. As illustrated, in one embodiment, sensor 52 is positioned adjacent system 21 and on a side opposite support 12. In addition, as illustrated, first sensor 50 is positioned between CT imaging configuration 14 and PET imaging configuration 16. Thus, sensors 50 and 52 are used to determine the heights of different table segments thereabove, the relative heights being identified by distances 80 and 82, respectively. Sensors 50 and 52 can take any of various forms including ultrasonic sensors, laser sensors, acoustical sensors, optical sensors, light sensors, magnetic sensors, and any other type of distance determining sensor known in the art.

Referring still to FIG. 2, data acquired by imaging configurations 14 and 16 is provided to compensator 40. Table position signals from sensors 50 and 52 are provided to determiner 42.

Determiner 42 uses the position signals to determine the relative positions of at least one and preferably both the of the CT and PET detectors with respect to table 18 during acquisition. To this end, the positions of the CT and PET detectors are always known as they are either stationary or the positions are precisely controlled. In addition, the positions of each of sensors 50 and 52 are known as the those positions are also fixed in the illustrated embodiment. Thus, the relative positions between each of sensors 50 and 52 and the CT detector 14 and the PET detectors 62 is known. Combining those known relative positions with the table positions from sensors 50 and 52, determiner 42 can easily determine the relative positions of the CT and PET detectors to table 18.

The relative positions are provided to compensator 40. Compensator 40 can be programmed to either modify the raw acquired data sets from the CT and PET detectors to compensate for the misalignment associated with distances 80 and 82, may compensate one set of the raw data, may compensate a final CT image prior to generating a unified image or may compensate both the final CT and PET images prior to generating a unified image. After compensator 40 modifies data to eliminate the affects of the misalignment, compensator 40 combines PET and CT images to generate a unified image which is then provided to interface 30 for review by a system user.

Referring now to FIG. 3, a method 100 according to the present invention is illustrated. Referring also to FIG. 2, at process block 102 position sensors 50 and 52 are provided adjacent imaging areas 60 and 64 along translation axis 19. At block 104, a patient is positioned on table 18 and the table and patient are positioned with respect to CT detector 14. At block 106 the vertical positions of table 18 identified by numerals 80 and 82 are determined by sensors 50 and 52, respectively and those position signals are provided to determiner 42. At block 108 CT configuration 14 is used to collect CT data which is provided to compensator 40.

Next after CT data has been collected for the portion of the patient to be imaged, table 18 is extended further along axis 19 until the portion of the patient to be imaged is located within PET imaging area 64. This positioning of the patient with respect to the PET detector 62 is identified by block 110. Continuing, at block 112, the positions 80 and 82 of table 18 are determined again using sensors 50 and 52 and those position signals are provided to determiner 42.

At block 114 PET detectors 62 are used to collect PET data which is again provided to compensator 40. At block 116 the position signals received by determiner 42 are used to determine the relative positions of detectors 14 and 62 with respect to table 18 during each of the CT and PET acquisitions. Next, at block 118 the relative positions of table 18 are used to modify at least one of the CT or PET data sets, and, perhaps both of the data sets. Finally, at process block 120 compensator 40 uses the compensated or modified data to generate a unified image including both the CT and PET data which is then displayed on interface 30.

It should be understood that the methods and apparatuses described above are only exemplary and do not limit the scope of the invention, and that various modifications could be made by those skilled in the art that would fall under the scope of the invention. For example, as indicated above, the compensator 40 illustrated in FIG. 2 can be used to either modify one or both sets of raw acquired data. In the alternative, the compensator 40 can modify final CT and PET images prior to generating a unified image although such compensation may be less accurate than compensation involving raw data. In addition, it should be appreciated that the present invention could be carried out using one position sensor if the relative height of table end 20 (see FIG. 2) were known or if CT configuration 14 were relatively thin (e.g., a few millimeters).

To apprise the public of the scope of this invention, the following claims are made:

What is claimed is:

1. An apparatus for use with a dual imaging system including a first and a second imaging configurations to collect first and second image data sets, respectively, that define adjacent first and second imaging areas along a translation axis, respectively, and that included first and second imaging detectors laterally displaced from the axis, respectively, the first and second configurations fixed with respect to each other along the axis, the system positioned adjacent a table support that supports a table for movement through the imaging areas along the axis, the apparatus for compensating for downward table divergence at the extended end of the table that occurs during table extension, the apparatus comprising:

at least one sensor for sensing the amount that at least a first table segment diverges downward as the table is extended from the support and into the imaging areas;

a determiner for using the amount that the at least a first table segment diverges to determine the relative position of at least one of the first and second detectors with respect to the table during data acquisition; and a compensator using the at least one relative position to modify at least one of the data sets prior to the sets being combined to form a unified image.

2. The apparatus of claim 1 wherein the first configuration is a functional configuration for obtaining imaging data corresponding to a dynamic characteristic and the second configuration is a static configuration for obtaining data corresponding to a static characteristic.

3. The apparatus of claim 2 wherein the static configuration is positioned between the support and the functional configuration.

4. The apparatus of claim 3 wherein the sensor is positioned adjacent the functional configuration opposite the static configuration.

5. The apparatus of claim 4 wherein the at least one sensor is a first sensor and the apparatus further includes at least a second sensor that senses the amount that at least a second table segment diverges downward as the table is extended from the support and into the imaging areas and, wherein, the determiner also uses the amount that the at least a second table segment diverges to determine the relative position of at least one of the first and second detectors with respect to the table during data acquisition.

6. The apparatus of claim 5 wherein the second sensor is positioned between the functional and static configurations.

7. The apparatus of claim 6 wherein the compensator modifies each of the functional and static data sets prior to combining.

8. The apparatus of claim 7 wherein each of the first and second sensors senses the vertical position of the table with respect to a fixed reference point and the amount that each segment diverges indicates the reference point to vertical table position distance.

9. The apparatus of claim 8 wherein the sensors are selected from a group consisting of laser sensors, ultrasonic sensors, light sensors, optical sensors, magnetic sensors and resistive sensors.

10. The apparatus of claim 5 wherein the determiner determines the relative positions of each of the functional and static detectors with respect to the table and the compensator uses each of the relative positions to modify at least one of the data sets prior to the sets being combined to form a functional/static image.

11. The apparatus of claim 1 wherein the at least one sensor is a first sensor positioned adjacent the system and opposite the support and the apparatus further includes at least a second sensor positioned between the first and second configurations that senses the amount that at least a second table segment diverges as the table is extended from the support and into the imaging areas and, wherein, the determiner also uses the amount that the at least a second table segment diverges to determine the relative position of at least one of the first and second detectors with respect to the table during data acquisition.

12. A method for use with a dual imaging system including first and second imaging configurations to collect first and second image data sets, respectively, that define adjacent first and second imaging areas along a translation axis, respectively, and that include first and second imaging detectors laterally displaced from the axis, respectively, the first and second configurations fixed with respect to each other along the axis, the system positioned adjacent a table support that supports a table for movement through the imaging areas along the axis, the method for compensating for downward divergence at the end of the table that extends from the support during table extension and comprising the steps of:

sensing the amount that at least a first table segment diverges downward as the table is extended from the support and into the imaging areas;

using the amount that the at least a first table segment diverges to determine the relative position of at least one of the first and second detectors with respect to the table during data acquisition; and using the at least one relative position to modify at least one of the data sets prior to the sets being combined to form a unified image.

13. The method of claim 12 wherein the step of sensing includes providing a sensor positioned adjacent the system opposite the support.

14. The method of claim 13 wherein the step of sensing includes providing a first sensor adjacent the system and a second sensor adjacent the system.

15. The method of claim 14 wherein the step of providing the second sensor includes positioning the second sensor between the functional and static configurations.

16. The method of claim 12 wherein the step of using the amount that the at least a first table segment diverges includes the step of determining the relative positions of each of the first and second detectors with respect to the table and the step of using the relative positions includes using each of the relative positions to modify at least one of the data sets prior to the sets being combined to form a unified image.

17. The method of claim 12 wherein the the step of modifying includes modifying each of the first and second data sets prior to combining.

18. The method of claim 12 wherein the step of sensing includes sensing the vertical position of the first table segment with respect to a reference point.

19. An apparatus for use with a dual imaging system including a functional imaging configuration and a static imaging configuration to collect functional and static image data sets, respectively, that define adjacent functional and static imaging areas along a translation axis, respectively, and that include functional and static imaging detectors laterally displaced from the axis, respectively, the functional and static configurations fixed with respect to each other along the axis, the system positioned adjacent a table support that supports a table for movement through the imaging areas along the axis, the apparatus for compensating for table deflection during table extension and comprising:

a first sensor for sensing the vertical position of at least a first table segment as the table is extended from the support and into the imaging areas, the first sensor positioned adjacent the system opposite the support;

a second sensor for sensing the vertical position of at least a second table segment as the table is extended from the support and into the imaging areas, the second sensor positioned between the first sensor and the support;

a determiner for using the position signals from the first and second sensors to determine the relative positions of each of the functional and static detectors with respect to the table during data acquisition; and a compensator using the relative positions to modify at least one of the data sets prior to the sets being combined to form a functional/static image.

20. The apparatus of claim 19 wherein the static configuration is positioned between the support and the functional configuration.

21. A method for use with a dual imaging system including a functional imaging configuration and a static imaging configuration to collect functional and static image data sets, respectively, that define adjacent functional and static imaging areas along a translation axis, respectively, and that include functional and static imaging detectors laterally displaced from the axis, respectively, the functional and static configurations fixed with respect to each other along the axis, the system positioned adjacent a table support that supports a table for movement through the imaging areas along the axis, the method for compensating for table deflection during table extension and comprising the steps of:

providing first and second position sensors adjacent the imaging area and displaced along the axis for sensing the vertical positions of the table along the axis during data acquisition;

sensing the positions of table segments as the table is extended from the support and into the imaging areas;

using the position signals to determine the relative positions of each of the functional and static detectors with respect to the table during data acquisition; and using the relative positions to modify at least one of the data sets prior to the sets being combined to form a functional/static image.

22. An apparatus for use with a dual imaging system including a first and a second imaging configurations to collect first and second image data sets, respectively, that define adjacent first and second imaging areas along a translation axis, respectively, and that include first and second imaging detectors laterally displaced from the axis, respectively, the first and second configurations fixed with respect to each other along the axis, the apparatus comprising:

a table support positioned adjacent the system;

a table supported by the support such that one end of the table is extendable from the support for movement through the imaging areas along the axis, the extended portion of the table sagging downwardly as the table is extended from the support;

at least one sensor for sensing the amount by which at least one table segment sags as the table is extended from the support and into the imaging areas;

a determiner for using the amount by which the table segment sags to determine the relative position of at least one of the first and second detectors with respect to the table during data acquisition; and a compensator using the at least one relative position to modify at least one of the data sets prior to the sets being combined to form a unified image.

* * * * *